United States Patent [19]

Vincent et al.

[11] Patent Number: 5,658,298

[45] Date of Patent: Aug. 19, 1997

[54] LAPAROSCOPIC TOOL

[75] Inventors: Vernon L. Vincent; Frederick L. Coe, both of Santa Barbara, Calif.

[73] Assignee: INAMED Development Company, Carpinteria, Calif.

[21] Appl. No.: 479,624

[22] Filed: Jun. 7, 1995

Related U.S. Application Data

[63] Continuation-in-part of Ser. No. 149,330, Nov. 9, 1993, abandoned.

[51] Int. Cl.⁶ .................................................. A61B 17/00
[52] U.S. Cl. ........................... 606/139; 606/148; 606/151
[58] Field of Search ............................ 606/1, 139, 144, 606/145, 148, 151, 157; 289/17; 112/80.03, 169; 600/201, 204, 210, 214, 215, 217, 219, 237, 239, 242, 243

[56] References Cited

U.S. PATENT DOCUMENTS

| | | | |
|---|---|---|---|
| 2,738,790 | 3/1956 | Todt, Sr. et al. | 606/144 |
| 4,592,355 | 6/1986 | Antebi | 606/144 |
| 4,813,407 | 3/1989 | Vogen | 606/151 |
| 4,836,205 | 6/1989 | Barrett | 606/144 |
| 4,874,375 | 10/1989 | Ellison | 600/217 |
| 5,196,022 | 3/1993 | Bilweis | 606/148 |
| 5,211,649 | 5/1993 | Kohler et al. | 606/139 |
| 5,226,429 | 7/1993 | Kuzmak | 606/157 |
| 5,242,459 | 9/1993 | Buelna | 606/139 |
| 5,258,007 | 11/1993 | Spetzler et al. | 606/208 |
| 5,300,082 | 4/1994 | Sharpe et al. | 606/147 |
| 5,383,882 | 1/1995 | Buess et al. | 606/151 |
| 5,391,173 | 2/1995 | Wilk | 606/144 |
| 5,415,666 | 5/1995 | Gourlay et al. | 606/148 |
| 5,447,514 | 9/1995 | Gerry et al. | 606/151 |
| 5,501,654 | 3/1996 | Failla et al. | 600/204 |

FOREIGN PATENT DOCUMENTS

| | | | |
|---|---|---|---|
| 3504202 | 8/1985 | Germany | 606/151 |
| 20911 | of 1894 | United Kingdom | 600/243 |

*Primary Examiner*—Jeffrey A. Schmidt
*Attorney, Agent, or Firm*—Michael G. Petit

[57] ABSTRACT

A tool is described which is useful for tightening a band or ligature having a buckle end and a free end during laparoscopic surgery. The tool comprises outer and inner elongate, slidably mounted cylindrical members. The outer member, which is slotted, has mounted on the distal end thereof a member for grasping the buckle end of a ligature. The inner member has a grasping portion mounted thereon and projecting through a slot in the outer member which is suitable for releasably engaging the free end of the ligature. In practice, the free end of the ligature is brought around to encircle a tissue and passed through a conduit within the buckle portion of the ligature, much as one threads a belt end through a buckle prior to cinching tight and fastening. The buckle portion preferably has a tab projecting therefrom with a hole therein which accommodates the buckle grasping member on the end of the outer member. The buckle grasping member is preferably a post or stationary pin which is inserted into the hole in the tab on the buckle portion. The free end of the end of the ligature has a special site for receiving and releasably engaging the free end grasping portion (fork) of the tool. A manually induced sliding motion of the inner member with respect to the outer member pulls the free end of the ligature a fixed distance through the buckle until a locking member engages the ligature within the buckle preventing removal of the free end therefrom. The buckle grasping member and the free end grasping member can be in opposite positions on the tool if anatomical circumstances are better suited by the arrangement.

4 Claims, 2 Drawing Sheets

LAPAROSCOPIC TOOL

CROSS REFERENCE TO RELATED APPLICATIONS

This is a continuation-in-part of application Ser. No. 08/149,330, filed Nov. 9, 1993 now abandoned.

BACKGROUND OF THE INVENTION

1. Field of the Invention

This invention relates to laparoscopic tools for performing surgical procedures and, more particularly, to a tool useful for tightening a ligature through a laparoscopic cannula.

2. Reference to Copending Application

Reference is made to copending patent application Ser. No. 08/068,411 filed May 27, 1993 entitled "Universal Gastric Band" now U.S. Pat. No. 5,601,604 by one of the present inventors.

3. Prior Art

There are many occasions when it is necessary to place a strap, belt, or ligature around a tissue or a prosthesis to fix it in place. Such a ligature can take the form of a cable tie commonly used for bundling electrical wires or a band such as a gastric band for encircling a stomach. Recently, laparoscopic methods and tools have been developed which enable the placement of such ligatures around organs or tissues without the need for open surgery. Unfortunately, it is difficult to manipulate the ends of such ligatures through a laparoscopic cannula inasmuch as the cannulae are rarely more than 12 millimeters in diameter. Moreover, a 3-dimensional operation such as fastening a ligature around a tissue must be accomplished by viewing the actual procedure on a 2-dimensional screen. Thus, it is inherent in laparoscopic surgery that spacial relationships must be arduously learned through practice.

Special bands have been devised to encircle tissue such as the stomach. Such a band is described, for example, in co-pending U.S. patent application Ser. No. 08/068,411 to one of the present inventors (V. L. Vincent). This band, which is designed to encircle a portion of the stomach to control overeating, has been fitted with a buckling mechanism whereby the band can be locked in an encircling position around the stomach. A balloon portion of the band is then inflated to further compress the walls of the stomach as required to produce a stoma of the correct dimension. The gastric band or ligature is comprised of a tunnel/buckle end and a free end with a strap or body portion therebetween. The free end of the strap is passed through the buckle and pulled snug until a "head" component near the free end exits the buckle, effectively locking the ligature in an encircling position. This maneuver can be done with existing laparoscopic surgical instruments, using one instrument to hold a tab on the buckle and another to pull the strap through the buckle. However, this leaves open a wide range of possibilities as to what instruments are used; blunt forceps, sharp tipped dissecting forceps, gaspers or even closed scissors. Whatever the choice of prior art instruments, the possibility of damage to the closure components or the tissue exists.

Bands such as that described above are difficult to fasten in position around the stomach through a laparoscopic cannula for the stated reasons. After the free end of the band is passed through the conduit in the buckle portion, the free end must be pulled tight with respect to the buckle portion so that a locking means can engage the buckle. Such maneuvering of the free end through the buckle and pulling and tensioning the strap to pull the locking means through the buckle may result in damage to the strap or to the buckle, or to surrounding tissue. This is particularly true if one or both of the instruments used to tighten the band slip loose abruptly and puncture or otherwise injure surrounding tissue. It is therefore desirable to provide an instrument for tightening a strap laparoscopically and which will provide a smooth, in-line traction on the free end and eliminate the problems presented by prior art tools.

SUMMARY OF THE INVENTION

It is an object of this invention to provide a tool for tightening a band.

It is another object of this invention to provide a tool for tightening a band which is operable through a laparoscopic cannula.

It is still another object of this invention to provide a laparoscopic band tightening instrument which prevents accidental abrupt release of the portions of the band that are being tightened.

These and other objects of the invention will become apparent as we turn now to the description of the drawings and the preferred embodiments.

DESCRIPTION OF THE PREFERRED EMBODIMENT

Figure 1:
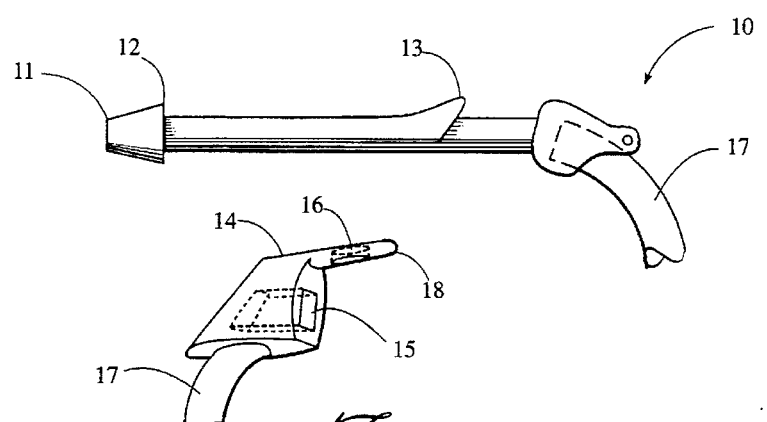
FIG. 1 shows a perspective view of a portion of a band having a buckle end, a free end and a locking portion which is suitable for tightening with the tool of the present invention.
Figure 2:
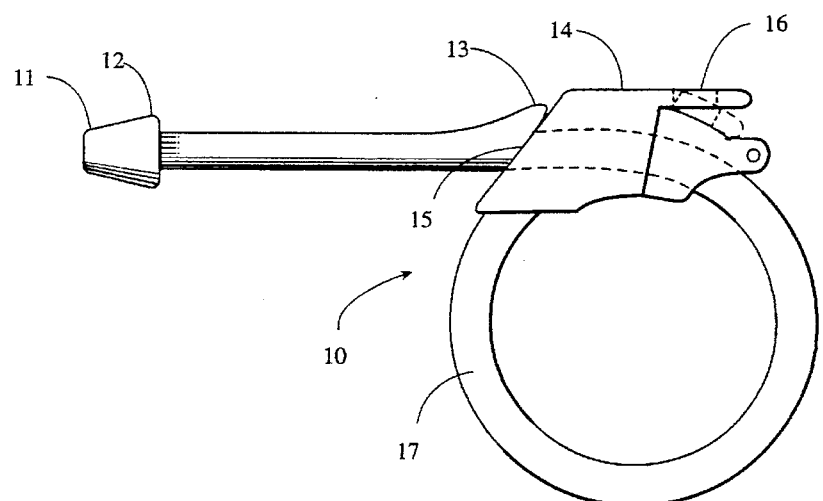
FIG. 2 is a side view showing the band of FIG. 1 locked in an encircling position.

A preferred embodiment of a band or ligature suitable for use with the band tightening laparoscopic tool of the present invention has been described in copending U.S. patent application Ser. No. 08/068,411 is shown at the numeral 10 in FIG. 1, without the internal inflatable sleeve. The band 10 has a distal end 11 having means thereon for grasping comprising protuberances 12 near the distal end 11 of the band 10. A locking means 13 engages a buckle 14 on the proximal end of the band 10 when the distal end 11 is pulled through the tunnel or conduit 15 within the buckle 14. A hole 16 in a tab 18 on the buckle 14 is dimensioned to receive a post on the distal end of the tool of the present invention. FIG. 2 shows the band 10 of FIG. 1 with the distal end 11 pulled through the conduit 15 within the buckle 14 until the locking means 13 engages the buckle 14 thereby locking a body portion 17 of the band 10 in an encircling position.

Figure 3:
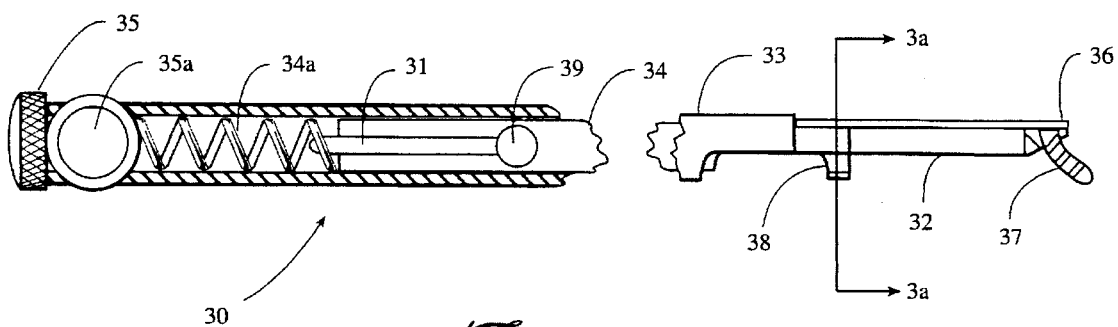
FIG. 3 is a cross sectional view of an embodiment of the laparoscopic tool of the present invention.
Figure 3A:
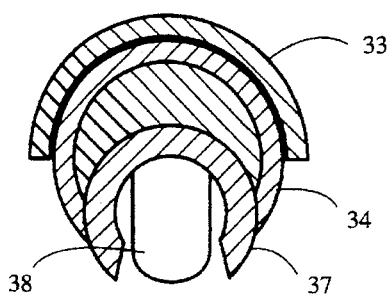
FIG. 3A is cross-sectional view of the laparoscopic tool of FIG. 3 taken along section line 3A—3A.
Figure 4:
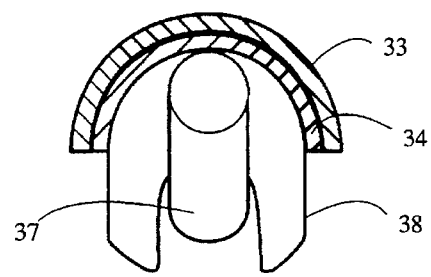
FIG. 4 is an alternate embodiment of the embodiment shown in FIG. 3A where the buckle grasping post and free end grasping seat have been interchanged.
Figure 5:
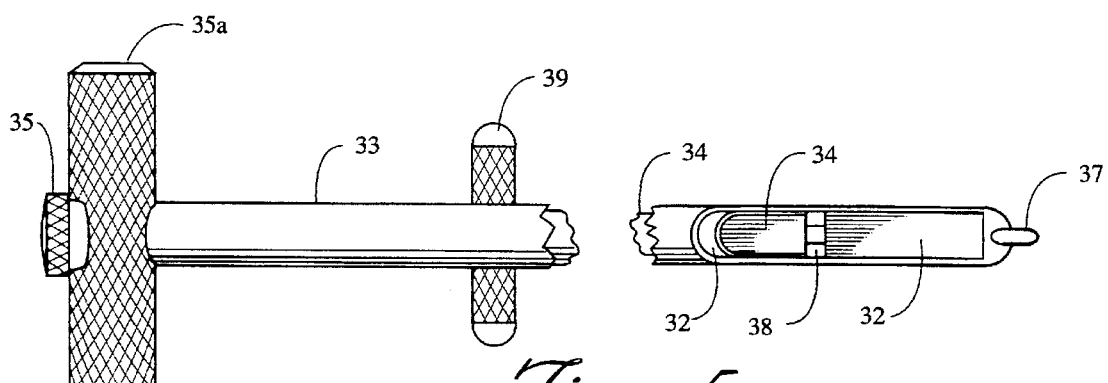
FIG. 5 is a bottom view of the laparoscopic tool of FIG. 3.

In FIG. 3 we see a tool according to the present invention. The tool, generally indicated at 30 comprises 2 cylindrical slidably-mounted members 33 and 34 and a handpiece 35 and 35a. At the distal end 36 of the tool 30 is a post or stationary pin 37. The length of the outer member between the handpiece 35a and the distal end 36 must be greater than the length of the laparoscopic cannula through which it can be inserted. The post or stationary pin 37 is dimensioned to engage the hole 16 in the tab 18 projecting from the buckle potion 14 of the band 10. The post or stationary pin 37 is preferably mounted on the outer cylindrical member 33. The inner cylindrical member 34, which is slidably mounted with respect the outer member 33, has mounted on its distal end a seat or fork 38. This fork 38, which is shown more clearly in the end view in FIG. 3A, is dimensioned to capture the protuberances 12 near the distal end 11 of the band 10. The seat or fork 38 travels in a first slot 32 in the outer member 33 (shown more clearly in the bottom view of FIG. 5). The outer tube 33 has a second slot 31 cut therein with a finger grip portion 39. The finger grip portion 39 is rigidly mounted to the inner tube 34. When the finger grip 39 is pulled toward the handpiece 35 and 35a, the fork 38 retracts away from the stationary pin 37. The relationship between the stationary pin 37 and the sliding fork 38 is seen more clearly in FIG. 3A in which the stationary pin 37 and the sliding fork 38 are shown in cross section along section line 3A—3A, and in the bottom view of FIG. 3. In FIG. 4 the post 37 and sliding fork 38 are reversed; the fork 38 being on the end of the instrument and the stationary pin 37 being mounted on the sliding inner member.

In practice, a band 10 is introduced into the abdomen through a laparoscopic cannula and manipulated into an encircling position around a tissue or other member (not shown) until the distal end 11 passes through the conduit 15 within the buckle 14. Normally, the conduit 15 within the buckle 14 will be dimensioned so that the distal end 11 of the band 10 will readily pass therethrough. The distal end 36 of the tool 30 is advanced through a laparoscopic cannula toward the buckle portion 14 of the band 10 where the stationary pin 37 is passed through the hole 16 in the buckle 14 to engage it. The sliding fork or seat 38 is maneuvered to engage the protuberance 12 near the distal end 11 of the strap. Traction is then applied to the finger grip 39 to pull the sliding fork 38 away from the stationary pin 37 thereby advancing the distal end 11 of the band through the conduit 15 in the buckle 14 until the locking means 13 passes through the conduit 15 in the buckle 14. The dimensions of the slots, particularly the length of the slot 31 in the outer tube 33, prevent further retraction of the sliding fork 38 with respect to the stationary pin or post 37. It is at this point that the barbed locking means 13 emerges from the conduit 15 in the buckle 14 thereby engaging the shoulder of the buckle 14 preventing retreat of the distal end 11 of the band 10 back through the conduit 15. At that point, the band cannot be removed from encircling position without cutting the band or a portion thereof.

Figure 6:
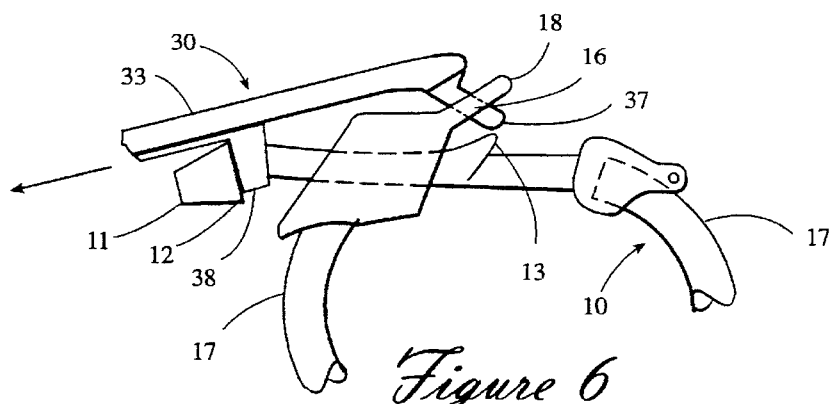
FIG. 6 shows a band according to FIG. 1 being grasped by a preferred embodiment of the tool of the present invention prior to being pulled into locked encircling position.

Returning now to FIG. 2, we see the band 10 in an encircling position. The band 10 is locked in this position because the backward slated or "barbed" locking means 13 is bigger that the conduit 15 in the buckle 14. This is seen more clearly yet in FIG. 6 which is a side view of the band 10 with the stationary post 37 and the fork or seat 38 of the tool 30 engaging the hole 16 in the tab 18 of the buckle 14 and the protuberance 12 respectively prior to the application of traction. After traction is applied in the direction of the arrow to pun the locking means 13 through the conduit 15, a spring 34a housed within the outer member 33 pushes on the inner member 34 and returns the fork 38 to its unretracted position in the slot 32.

In summary, the instrument disclosed herein consists of two simple structural features and one simple mechanical action. The first feature is a stationary pin. This pin is sized and shaped to allow it to be inserted into a receiving hole or slot in a tab feature of the buckle component of a ligature. The second structural feature is a fork, seat or "U" shaped extension. This feature provides a concentric lock-ring type on a flared bump or raised shoulder on the strap. The fork and pin are located at the tip of the instrument and at some distance from the tip on the end of the inner concentric member respectively and interchangeably.

Figure 7:
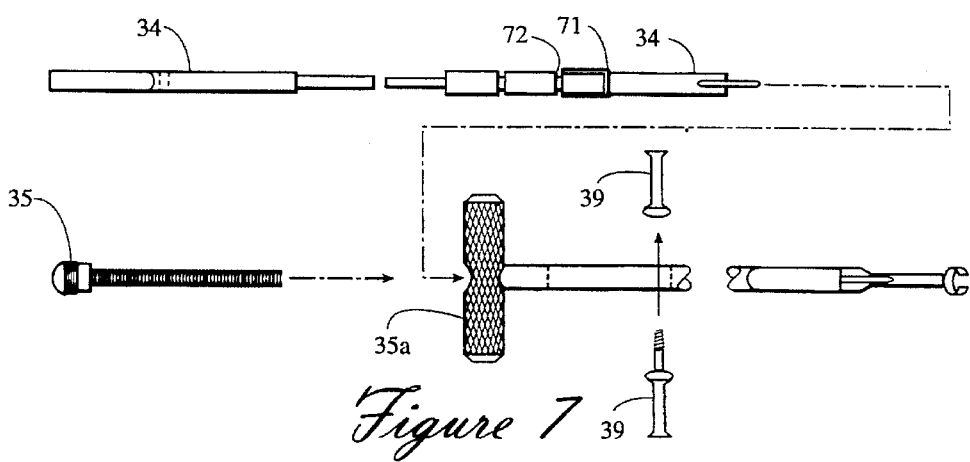
FIG. 7 is an exploded view showing the structural relationship between the parts of the tool.

The above-described tool is designed and intended for laparoscopic use. Laparoscopy is a surgical technique in which a surgical field is created within the abdomen, a closed body cavity, by inflation of the cavity with a gas, usually $CO_2$. The insufflation process creates a pneumoperitoneum. Surgical instruments are inserted into this cavity through air tight seals on trocar cannulas, tubes which provide access to the surgical field. For the pneumoperitoneum to be maintained, the instruments must fit through the cannulas in such a way that very little gas escapes from the abdomen. In addition to the cannula seal, any instruments projecting therethrough must prevent gas from escaping through the instrument; i.e. along an internal channel or past connections. The tool must be "air-tight" to prevent gas from escaping from the cavity through the instrument. The inner shaft of the tool is a solid rod. Gas cannot escape through it. Significant gas loss could occur if sufficient space existed between the outside wall of the inner shaft and the inside wall of the outer shaft. The tolerances of both shafts are set to prevent gas from the inflated cavity from escaping through the space between the inner and outer shafts. As an additional safeguard for preventing deflation of the cavity during use of the present invention, an o-ring 71 (FIG. 7) encircling the distal end of the inner shaft 34 is positioned in an annular groove 72 to further occlude the space between the inner and outer shaft.

The tool's 30 closure mechanism has slots 31 in the wall of the outer shaft which serve as a pre-set stop to limit the range of travel of the inner shaft. The length of the slots 31 on the side of the outer shaft prevent advancement of the finger grip portion 39 of the inner shaft therebeyond. Damage to the band being implanted due to over tightening is thereby avoided. The slots prevent overtightening of the band during fastening. The buckle and belt configuration of an implantable gastric band, for example, can be damaged by the application of excess force or excessive stretching. Two individual instruments, or a prior art band tightening tool similar to the tool of the present invention but lacking such adjustable travel means, could generate opposing forces that could stretch the fastening components of the implant excessively, tearing or irreversibly deforming the elastomeric components. The slots in the outer shaft limit the travel, making it impossible for the proximal hook to be pulled too far from the distal fork but far enough to fasten the band.

The chance of inadvertent damage or injury to surrounding tissue is minimized by the controlled, low-force sliding movement of the inner shaft within the outer shaft. Because the travel distance of the inner shaft is limited, there are no residual forces that could cause the hook or fork to slip off or tear out of the banding device's closure/locking components. The inherent risk of slipping and resultant tissue trauma associated with two instruments grasping and "tugging" in opposing directions in a lubricious environment, is avoided.

The instrument is simple to use. The closure mechanism of a strap or ligature is engaged and tightened manually with conventional instruments up to the point that the closure mechanism is almost engaged and snug in the buckle conduit. The stationary pin of the instrument is inserted into a hole or slot in a tab on the top, back or face of the buckle. The leading end of the strap that has already passed through the buckle will have a flared bump or raised shoulder on it. The notch feature of the instrument is positioned so that it will be the correct distance from the tip and buckle tab interface such that the notch can be positioned directly over the bump or shoulder on the strap. The strap may be manipulated with a conventional forceps to engage the strap into the receiving notch. Following engagement the mechanical action of the instrument consists of one moving column. When the mechanism is activated, the buckle post moves away from the notch, or vice-versa. The result is a controlled, even, in-line pulling of the strap locking head through the buckle conduit. The travel of the inner sliding member is regulated so that the buckle cannot be over-tightened, pulling the head through just far enough to clear the buckle conduit. Upon releasing the closure mechanism, the strap can be disengaged from the gripping notch with any conventional blunt laparoscopic instrument. The buckle post is then simply pulled back out of the tab hole and the instrument is removed from the surgical field through the port of the cannula.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A device operable for tightening a ligature through a laparoscopic cannula wherein the ligature is an elongate strap which has a buckle end and a distal end, the distal end having a protuberance projecting laterally therefrom, and a body portion therebetween and wherein the buckle end has a post receiving hole thereon and an aperture therethrough wherein the aperture is adapted to slidingly and lockingly engage the distal end of the ligature, the device comprising:

(a) an outer elongate tubular member with a cylindrical channel formed therethrough, wherein at least a portion of said outer elongate tubular member is dimensioned to enter one end, pass through and extend beyond the other end of the laparoscopic cannula, said outer elongate tubular member having a distal end with a fork projecting therefrom and wherein said fork is adapted to engage the protuberance in the distal end of the ligature; and (b) an inner cylindrical member having a distal end with a blunt post projecting therefrom, said post being dimensioned to engage with the blunt post receiving hole in the buckle end of the ligature, said inner cylindrical member being concentrically, slidingly, and substantially air-tightly mounted within said cylindrical channel of said outer tube such that said distal end with said blunt post extends distally through and substantially beyond said fork of said outer elongate tubular member.

2. The device of claim 1 further comprising means operable for slidingly manipulating said inner cylindrical member with respect to said outer elongate tubular member through a preset travel distance.

3. The device of claim 1 wherein an O-ring is used to provide substantial air-tight sealing between said outer elongate tubular member and said inner cylindrical member.

4. The device of claim 1 further comprising a spring means to bias said inner cylindrical member forwardly with respect to said outer elongate tubular member.

* * * * *